United States Patent
Soules (10) Patent No.: US 6,727,690 B2
(45) Date of Patent: Apr. 27, 2004

(54) TEST METHOD FOR DETERMINING IMMINENT FAILURE IN METALS

(76) Inventor: Jack Arbuthnott Soules, 3009 Van Aken Blvd., Shaker Heights, OH (US) 44120

( * ) Notice: Subject to any disclaimer, the term of this patent is extended or adjusted under 35 U.S.C. 154(b) by 0 days.

(21) Appl. No.: 10/224,776

(22) Filed: Aug. 20, 2002

(65) Prior Publication Data

US 2004/0036470 A1 Feb. 26, 2004

(51) Int. Cl.$^7$ .............................. G01B 7/24; G01R 33/18
(52) U.S. Cl. ........................ 324/209; 324/242; 73/779
(58) Field of Search ................................ 324/240, 232, 324/234, 237, 238, 207.16, 209, 239–243; 73/12.01, 12.04, 12.09, 841, 779

(56) References Cited

U.S. PATENT DOCUMENTS

| | | | |
|---|---|---|---|
| 5,610,515 A | | 3/1997 | Soules |
| 5,698,977 A | * | 12/1997 | Simpson et al. ............. 324/209 |
| 5,744,954 A | | 4/1998 | Soules |
| 5,898,302 A | * | 4/1999 | Soules ......................... 324/209 |
| 6,294,912 B1 | * | 9/2001 | Kwun ......................... 324/240 |

\* cited by examiner

Primary Examiner—N. Le
Assistant Examiner—Subhash Zaveri
(74) Attorney, Agent, or Firm—Alfred D. Lobo (57) ABSTRACT

A method for determining a "safe-operation" point for a metal structural element subjected to repeated loading, the same or different, generating variable levels of strain and residual stress in the worked element; and, predicting the imminent failure of the structural element. The surface of the metal element is worked to provide a residual strain, for example, by shot-peening. Measurements of electrical conductivity are compared at various chosen frequencies corresponding to different depths in the "near-surface" of the element. Similar measurements are made in the near-surface of a "standard" and a first difference is computed between the conductivity of the shot-peened surface and the "standard" surface. This first difference provides a basis for comparison of the effects of residual stress after successive loadings of the shot-peened metal element. The effect of residual stress on the peened portion after it is subjected to a number of successive loadings is measured and compared to the reference. When the effect of residual stress is measured as conductivity or resistivity, it is found that there is a progressive increase in conductivity (and decrease in resistivity) as the metal element begins to succumb to fatigue. It is found that when the resistivity decreases to a value in the range from about 50% to 60% of the measured first difference in resistivities, the metal element has reached its 50% "safe-operation" point beyond which it rapidly, progresses to fatigue failure.

20 Claims, 3 Drawing Sheets

TEST METHOD FOR DETERMINING IMMINENT FAILURE IN METALS

FIELD OF THE INVENTION

This invention relates to a method of testing a metal structural element, using precise measurements of eddy currents generated on the surface of the structural element being tested, to determine the useful life of the structural element without destroying it. Such eddy currents are induced in a mass of conducting material by a varying magnetic field.

BACKGROUND OF THE INVENTION

Metal structural elements of a vast array of devices are routinely subjected to severe stresses under which they are designed to operate over the endurance life of the devices. Such stresses are caused by forces producing, or tending to produce deformation in a device or a portion of it; the stresses are measured by the force applied per unit area, for example as dynes per square centimeter (or pounds per square inch); the forces are typically axial torsional or bending. To increase their service life, metal structural elements of ferrous metals, aluminum, titanium and other metals which are susceptible to an increase in residual compressive stress at the surface when peened or shot-peened, are routinely shot-peened, which delays fatigue failure.

Fatigue refers to the failure of materials under the action of repeated stresses; it is responsible for a large proportion of the failures occurring in any one of a myriad structural parts of an aircraft, wheels of heavy duty trucks and rail cars, and a wide array of machine parts. But the expected service life of any of the structural parts is purely conjectural; the expected life is typically estimated from prior experiences with actual failures, or by destructive testing of an essentially identical device, such testing being carried out under what is believed to be the same spectrum of stresses to which such devices are expected to be subjected.

Typically, a series of fatigue tests are carried out on a number of specimens of a particular structural element at different stress levels, until each specimen fails; the stress endured by each specimen is then plotted against the number of cycles sustained. For steel structural elements, choosing lower and lower stresses, a value for stress may be found which will not produce failure even after a very large number of cycles. This stress value is termed the "endurance limit" and the diagram is referred to as a stress-cycle diagram or S-N diagram. In structural elements made of aluminum alloys, the build up of residual stress is more cumulative than in steel and less predictable. In the design and construction of devices where weight and cost are critical, designing a device to operate at stress values low enough to produce the endurance limit is not an option; the goal is the opposite, namely to design a device to operate at as high a stress value as will fall just short of the endurance limit.

For example, the landing gear of an aircraft is designed to operate for some predetermined period of time under preselected operating conditions. Failure of a critical strut in the landing gear under a chosen cyclical load, can be observed when the strut breaks. For the chosen strut, and every other structural element, there is a combination of peak load and number of cycles which provides a 50% failure point, that is, the point at which 50% of all the parts tested will have failed under those test conditions. In the field, an engineer does not know what peak load a particular part has endured, nor, typically, the number of cycles. Therefore the time when the part will fail during its normal operation is unpredictable.

Assuming one was to test a single strut, from a batch of many essentially identical struts which had been in similar service, until that strut failed, the test information might be used to predict the useful life of the remaining struts. Unfortunately, one cannot predict with reasonable certainty, the period after which a strut on the landing gear of an aircraft will fail after the aircraft is placed in service. Landing gear, typically of aluminum or titanium, is designed to withstand the forces generated by that aircraft not only while it is at rest, or while it is hurtling down a runway prior to take-off, but also when it lands. As is well-known, each landing is different from another, some, for example those on a pitching deck of an aircraft carrier, generating stresses an order of magnitude (ten times), or more, greater than those on a deck of the carrier on a calm sea. It therefore is imperative that the aircraft and its landing gear be removed from service well before its imminent fatigue failure. Knowing when to do so, until the discovery disclosed herein, has not been possible.

It should be recognized that, were it possible to identify precisely, the 50% failure point for a structural element which was still in service, the identification, in reality, would have been too late, because by definition, there was a 50% probability that the structural element would have already failed.

A structural element such as a strut of a ferrous metal or any other structural element of a device or machine may be checked by magnafluxing the element, which requires a large enough disturbance of the magnetic flux to allow the magnetic powder to gather in the vicinity of a non-uniformity, such as a crack. When this occurs the accumulation of residual stresses in the part has already reached or exceeded a "safe-operation" point where failure of the part is imminent, that is, the accumulation has progressed too far to allow the device to be operated safely. An accumulation of stresses past the "safe operation" point may also be observed in steel and aluminum devices with dye penetrants commercially available in "spot check" kits.

Checking the structural element by X-ray provides information relating to a change in strain as evidenced by changes in a diffraction pattern from surface atoms, where there is displacement of atoms or distortion of grain structure, to a depth limited to less than 50 $\mu$m (microns), typically less than 20 $\mu$m, and often as little as 10 $\mu$m. Seeing such variations provides no information as to how many stress cycles the structural element has endured, nor the magnitude of the strain. If, just before the X-ray measurements are made, the sample has relaxed its accumulated internal strains sufficiently so as "to report" normal atomic spacing, the conclusion derived from such information, though an excellent method for determining the condition of the element at that particular time, would be misleading. Moreover, X-ray measurements are too costly and time consuming, therefore generally impractical.

The Problem: In the example of the landing gear just provided, over the course of several years, it is presently not possible to make an educated, economical appraisal of the condition of any of its structural elements at any time after it has been in service, and no method of determining how close to failure that element might be. If one could predict that a stressed component of any device would fail within a specified window of time, assuming operation of the device was continued, then, without otherwise interrupting operation of the device, that component could be taken out of service no later than, and preferably before the prediction indicated that the component had reached a "safe-operation" point, despite the component appearing to be in good condition. The problem is to find a method which allows one to make that prediction with reasonable accuracy.

U.S. Pat. No. 5,610,515 teaches a method of measuring eddy currents modified by residual stress in non-ferromagnetic metal objects, using certain circuit elements in an alternating current circuit the values of near-surface residual stress can be inferred. Generated eddy currents measured are modified by near-surface compression or tension resulting from working the surface for example, by shot-peening it, or by rolling material from which a structural element is fabricated. The term "near-surface" refers to a superficial zone having a depth in the range from about 0.025 mm (0.001") to 0.5 mm (0.020") for structural elements in the range from about 3 mm to 8 mm thick; for thicker elements up to about 25.4 mm thick the depth of the near-surface extends to a depth of about 0.75 mm (0.030"), the depth generally increasing proportional to the thickness. The "non-destructive" test method, so termed because no damage is inflicted on the specimen, provided an indication of the level of residual stress at the surface where the measurement was made. Such detection was more effective than when, in the past, the likelihood of such a macroscopic defect was tested by stressing the specimen with a large, but not excessive force, sufficient to enlarge the defect but not destroy the specimen insofar as its intended use was concerned. There is no suggestion in the '515 reference that tracking sequential changes in conductivity or impedance might be used to predict failure of the sample under continued stress.

U.S. Pat. No. 5,744,954 teaches a method of measuring physical properties in ferromagnetic metals by limiting the magnetic field strength of the test coils. It was recognized that a wide variety of physical properties in a metal object will be altered with heat treatment, for example, as well as resulting from fatigue or residual stress. It was also recognized that existing eddy current measurement techniques were incapable of detecting small conductivity changes even in so-called "perfect" metals lacking material or structural imperfections. Moreover, the '954 patent contemplated using its measurement procedure to measure metal fatigue as well as physical condition after heat treatment, but offered no suggestion as to how this might be done.

U.S. Pat. No. 5,898,302 teaches a method of measuring residual stress in both ferromagnetic and non-ferromagnetic metals by measuring small imbalances in a bridge having four electrically identical induction coils which form a four terminal alternating current bridge circuit. Because the position of the coils on the metal surfaces is not changed, there is no "lift-off", and because the conductivities being measured are nearly the same, the difference measured is readily visible. This method detects very small changes in conductivity between a treated metal object which is worked sufficiently to produce a change in its metallurgical structure, which change is sensed and measurable as resistivity differences. These resistivity differences, attributable to the displacement of atoms or grains of the metal, are converted into residual stress. Different levels of residual stress may then be compared. Prior to the '302 patent, the eddy current measurements detected relatively macroscopic defects not easily visible, or compositional variations in non-ferromagnetic metal objects. Using appropriate induction coils in the procedure taught in the '302 patent, one can detect a change in conductivity due to stress corresponding to a change in impedance of the coils in the range from 0.01 to 0.001 percent, typically as small as 0.006 percent.

It is well known that stressing the near-surface of a metal article, for example by shot-peening the surface, provides protection to the extent that the residual compressive stress must be overcome by deformation of the surface before additional deformations cause the article to be so fatigued as eventually to fail. Typically the near-surface of an aluminum element from 3 mm to 6 mm thick is peened, or shot-peened to a depth in the range from about 0.127 mm (0.005") to 0.381 mm (0.015").

At the present time, structural elements such as aircraft and truck wheels, spars in the wing of an aircraft, brackets on locomotive wheels, and numerous other elements are surface-stressed for added protection. During the operating life of the structural element, e.g. an aluminum wheel, it is periodically inspected in annular zones known from experience to have a proclivity for failure. Such zones may be different for different wheels of different vehicles but typically include a first zone around the bolt holes, a second zone around the central opening in which an axle is held, and a third zone near where a tire's bead is secured on the rim. As of this date, when a tire is demounted from the wheel for inspection of both, one or more of the annular zones is typically treated with a dye-penetrant and visually inspected. A visible indication of an incipient fissure, or worse, a crack, is cause to remove the wheel from service. However, either the incipient fissure or the crack is each an indication that failure due to fatigue has already occurred. The critical inspection was made too late because both, the additional protection provided by the shot-peened surface as well as that of the wheel after the added protection provided by shot-peening was used up, have been negated. With luck, the wheel is inspected and removed from further service before a catastrophic accident.

Methods of using eddy currents to compare precisely the electrical conductivity in a shot-peened surface to that of a similar, unpeened surface are disclosed in "Non-destructive Residual Stress Measurement Using Eddy Current", by Hong Chang, Fred C. Schoenig, and Jack A. Soules, Sixth International Conference on Shot-Peening, San Francisco, Calif., 1996; "Advances in Eddy Current Measurement of Residual Stress", by D. Barac, W. Katcher., and J. Soules, Seventh International Conference on Shot-Peening, Warsaw, Poland, 1999; and "Eddy Current Offers a Powerful Tool for Investigating Residual Stress and other Metallurgical Properties", by Hong Chang, Frederick C. Schoenig, Jr., and Jack A. Soules, Materials Evaluation, Vol. 57, No. 12, December 1999.

The accuracy of the foregoing methods allows one to observe the effect of repeated heavy loading on the surface conductivity of a metal article and dispenses with magnafluxing or using a dye penetrant.

SUMMARY OF THE INVENTION

Repeated loading of any metal article causes fatigue which, in turn, produces displacement of atoms, distortion of grain boundaries, work hardening and other metallurgical effects which may be sensed and quantified, for example by changes in X-ray diffraction patterns, or by changes in electrical conductivity. In particular, such effects are measurable as electrical conductivity. In a bent specimen, stress is largest in the near-surface where conductivity measurements may be made with precision.

Repeated cyclical loading of a metal structural element generates irregular and unpredictable variations of conductivity. Measurements of such variations cannot be used either to evaluate fatigue of a specimen being tested, or to predict its 50% failure point. However, by superimposing a superficial compressive stress in the near-surface of a zone prone to failure, for example, by working the near-surface of the specimen until it has a chosen level of residual stress, e.g. by peening, preferably shot-peening a portion of the specimen's surface, and monitoring the conductivity (or resistivity) in that portion over a number of cycles of externally applied stress until the difference is about 50% to 60% of the difference between the initial resistivity at the chosen level of residual stress and a reference "standard", it is unexpectedly found that this difference is correlatable to the "safe-operation" point beyond which loading and unloading of the specimen progressively increases the risk of actual fatigue failure.

Assuming failure due to fatigue in an aluminum wheel of an aircraft's landing gear is known to occur first in the third annular zone (the wheel's rim near where the bead of the mounted tire is secured), by shot-peening a portion of the zone to a chosen extent, then measuring the difference in resistivity in that portion and a "standard" sample, a "base" value is obtained. After the wheel has been in service for a period during which the aircraft has been in service, the same shot-peened portion is measured to obtain the difference in resistivities between that portion and the "standard" sample. By monitoring this difference over a prolonged period of operation of the aircraft, the imminent failure of the wheel may be predicted and the wheel removed from service at some chosen time when the difference in resistivities has reached a predetermined value, typically in the range from 50% to 60% of the original or base value.

In an analogous manner, a spar in an airplane wing is shot-peened in a zone known to be likely to fail first when the spar has been unduly fatigued, which zone is marked for easy identification. The difference in resistivities between that shot-peened portion and a "standard" sample is monitored over the life of the aircraft to ensure that the difference in resistivities has not diminished more than 50% to relative to that difference between the peened portion at the beginning and the "standard" sample.

BRIEF DESCRIPTION OF THE DRAWING

The foregoing and additional objects and advantages of the invention will best be understood by reference to the following detailed description, accompanied by an illustration of a test apparatus, and with graphs in which.

DETAILED DESCRIPTION OF PREFERRED EMBODIMENTS

Fatigue failure begins at the surface and propagates into and through a structural element of an article, or device, or a specimen, under load. The goal is to measure the difference in at least one of the properties of the stressed near-surface of a first structural element which has been subjected to loading and a reference "standard" near-surface of a second structural element, metallurgically essentially identical to the first, irrespective of the particular means for making the measurements. The "standard" is most preferably stress-relieved until there is substantially no measurable residual stress in the near-surface. However, if desired, the standard may also be worked, for example by shot-peening, until there is a known residual stress which will be the reference standard used to make a comparison. The structural element or specimen to be tested for fatigue is typically subjected to a multiplicity of sequential loads, and at chosen intervals, the change in a property which has a one-to-one correspondence with strain, is measured. Most preferably the difference in electrical conductivity between the test specimen and the standard is measured at intervals, either of time or of number of cycles of loading and unloading, the length of the intervals and the number of cycles in each interval depending upon the test specimen and the type of service.

The goal is to identify a "safe-operation" point for any structural element, which point indicates that the structural element has served the major portion of its safe, useful life. By providing an indication of the remaining interval, either of time or the number of loading and unloading cycles, before actual failure, the risk of operating with the structural element beyond the "safe-operation" point may be estimated.

The goal is therefore to quantify and compare the sensed difference in at least one property measurable in the near-surface of a treated or "worked" metal structural element or component of a device, and in the near-surface of an untreated or "standard" metal structural element used as a reference. The operability and effectiveness of the method hinges upon measuring and comparing at least one property of the near-surface to determine a first difference between a first measurement of residual stress in the near-surface of the first metal structural element, and, a reference measurement of a reference residual stress in the near-surface of a standard metal structural element having essentially the same metallurgical properties as the first when each is stress-relieved; repetitively loading the first metal structural element; measuring and comparing the property of the near-surface to determine differences between each measurement of residual stress in the near-surface of the first metal structural element after each loading, and the reference measurements at corresponding depths in the near-surface; and, determining the 50% safe-operation point for the first structural element corresponding to an Nth loading for which the difference between the residual stress at the Nth loading and the residual stress in the standard reference metal structural element is in the range from about 50% to 60% of the first difference.

The property to be sensed is preferably conductivity (or resistivity) which is converted with an algorithm into a value of residual stress. If the unstressed (not shot-peened) standard is assigned a reference value of zero, then shot-peening produces the maximum difference in resistivities between that corresponding to the residual stress of the shot-peened surface and the reference resistivity of zero. This maximum difference is measured as a first difference in resistivity. As the test component is further worked by repetitive loading, the conductivity increases and the resistivity decreases indicating that the residual stress in the shot-peened surface is decreasing. When the difference in resistivity differences (which correspond to residual stress values) between the shot-peened surface which is still further worked by additional loading, and that of the reference decreases to a value in the range from about 50% to 60% of the value of the first-measured difference, a prediction that the test component has reached its "safe-operation" point is found to be accurate. This is confirmed by actual fatigue failure soon after the value reaches its maximum.

Figure 1:
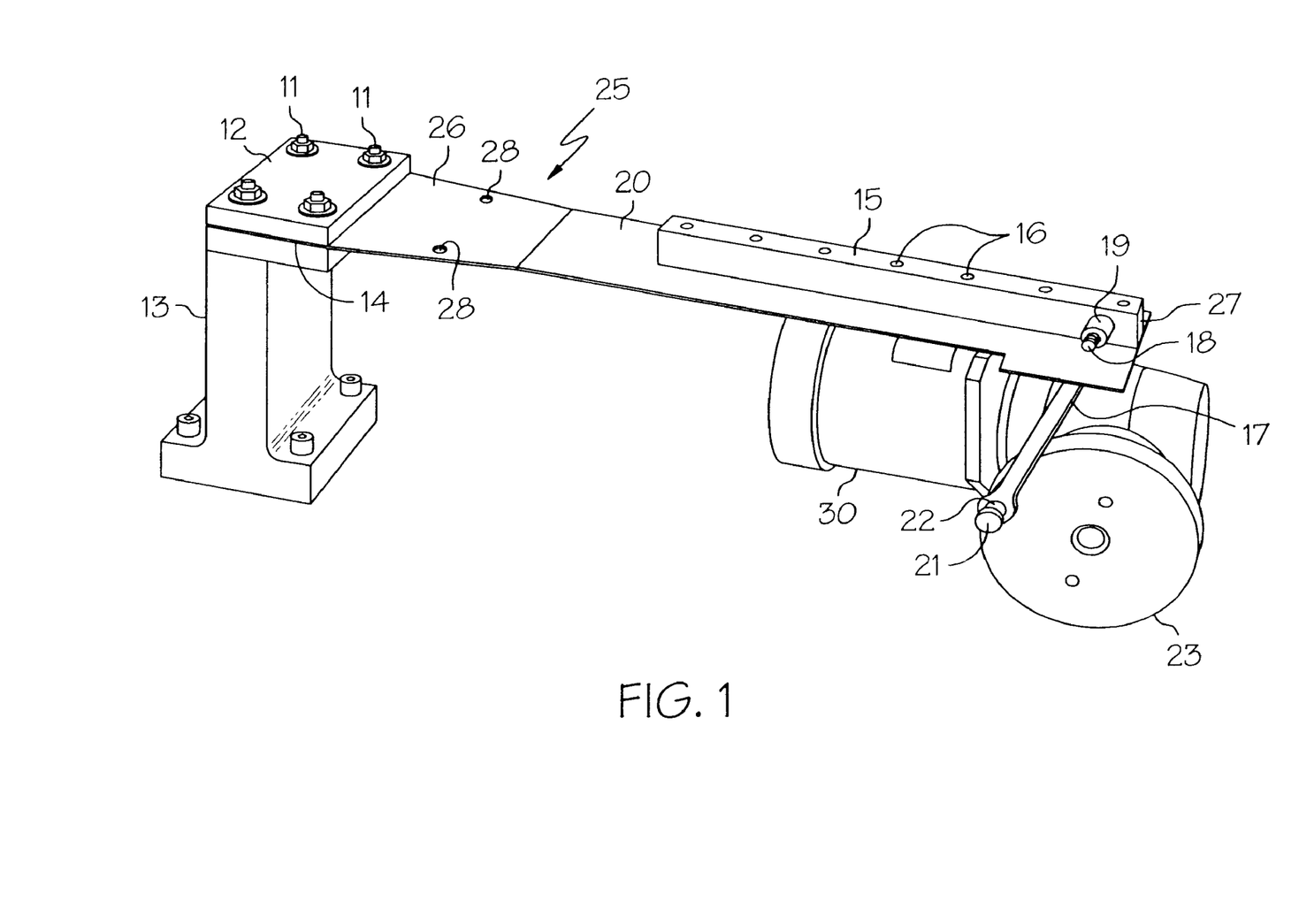
FIG. 1 is a schematic illustration of a test apparatus used to repetitively load a plate of aluminum.

For simplicity, an elongated laminar plate is used as the specimen to be tested. Because, unlike steel, aluminum stores residual stress at relatively low levels relative to the 50% fatigue limit, the specimen chosen is an aluminum plate, and 2024 aluminum is chosen because this alloy is relatively common. Schematically illustrated in FIG. 1 is a simple test machine referred to generally by reference numeral 10, constructed to deform a plate 20 cyclically to produce appropriate, successively greater fatigue in the plate, to a maximum surface stress of about 103 MPa (megaPascals) (that is, 25 Ksi (thousand pounds per square inch)) tension, and about 103 MPa (15 Ksi) compression. The plate 20, about 43 cm long, 10 cm wide and 4 mm thick, is releasably tightly secured near its one end with four machine screws 11 in through-bores at corners of a clamping plate 12, the screws being threaded into the upper portion of a rectangular post 13. The longitudinal axis of the clamped plate is normal to the upper transverse edge 14 of the post 13, which edge 14 is under the plate and in contact with it.

To stress the plate by bending it with a force applied near its other end, and to ensure that the stress is applied mainly in a zone near the clamped end of the plate, a stiffening bar 15 of aluminum, about 15 cm long and having a cross-section of about 1.5 cm square, is bolted with machine screws 16 longitudinally along the center axis of the plate, one end 27 of the bar 15 terminating above the edge of the far end of the plate.

The end 27 of the bar 15 is pivotably connected to one end of a rod 17 which functions as a crank-arm, with a bolt 18 through a first rod-bearing 19 on one end of the rod 17, the other end of which rod is connected with a second rod-bearing 21 journalled on a bolt 22 threaded into a rotatable disc 23 functioning as a crank to lower and raise the rod 17 and the end of the bar 15 to flex the plate 20. The disc 23 is driven by a variable speed electric motor 30. The radial distance at which the rod-bearing 21 is pivotally connected to the disc 23 may be changed to provide different degrees of flexure; and the disc 23 is driven relatively slowly, in the range from about 0.5 to 2 revs/sec, preferably 1 rev/sec, to maintain essentially constant temperature in the stressed plate.

A portion 25 of the zone near the clamped end of the plate 20 is shot-peened across the width of the plate over a distance of about 3.5 cm along the longitudinal axis, to produce approximately a 9A intensity per MIL13165C. This results in a distribution of compressive stress to a depth of about 0.25 mm, with the greatest stress in the near-surface diminishing to neutral at about 0.30 mm to 0.37 mm. To ensure that the plate will fail near the midpoint of the shot-peened zone it is notched by drilling a pair of 3 mm diameter holes 28 near the longitudinal edges of the plate, the holes being directly opposite each other. The near side 26 (nearest the post 13 of the shot-peened portion 25 is about 6 mm from the edge 14 to ensure that flexure of the plate is concentrated in the shot-peened zone. Peak stress and ultimate failure will occur in the shot-peened portion where measurements of residual stress are to be made, along a line connecting the two holes.

It will be appreciated that the peening or shot-peening of the surface introduces a desirable level of compressive stress in the near-surface. The extent of the peening will depend upon the thickness of the metal structural element and its composition. Experience dictates that the same thickness of steel, aluminum and titanium will be shot-peened differently for optimum results.

In the first set of data presented herein, measurements are made on the surface of an unstressed "standard" 2024 aluminum plate, used as the reference, which is stress-relieved and not shot-peened. Another stress-relieved and unpeened (or not-shot-peened) 2024 aluminum plate is then cyclically stressed, at chosen intervals, sequentially, and measurements made and compared directly to determine the difference in conductivities between the stressed plate and the standard (or, the difference in resistivities), without requiring that the conductivity of either be quantified.

To stress the specimen, it is clamped in the test machine as described, and is subjected to 20,000 cycles, after which the difference in conductivities between the stressed portion and the standard surface is measured. This specimen is then subjected to an additional 10,000 cycles and the conductivity in the stressed portion is again measured. A progressive decrease in surface conductivity is evidence that there is an increase in residual stress produced in the specimen.

This stressed sample is then subjected to additional thousands of cycles, stopping periodically to measure conductivity in the stressed portion. After several thousands of cycles, the conductivity rather suddenly increased, tending toward the original state. The accumulated energy was relieved as the material relaxed. Then the cycle is repeated, building up residual stress (lower conductivity) and relaxing. The measured conductivities provide a sawtooth pattern which is unpredictable because the episodes of relaxation occurred randomly, after several tens of thousands of cycles.

The data is collected by recording the difference in voltage across the test coil on the "standard" and the voltage across the test coil on the strained test material. This difference in voltage varies in both magnitude and phase as compared to the voltage applied to the bridge. The comparative conductivities are reflected in both the amplitude and the phase of the voltage difference. The resulting data was plotted as a function of frequency to produce a chaotic pattern of curves, a result of the effect of dynamic metallurgical phenomenon such as dislocation movement and "stick-slip phenomenon". The data represented by the apparently random curves were difficult to interpret in that form, though one with much experience in reading such curves may be able to do so.

Figure 2:
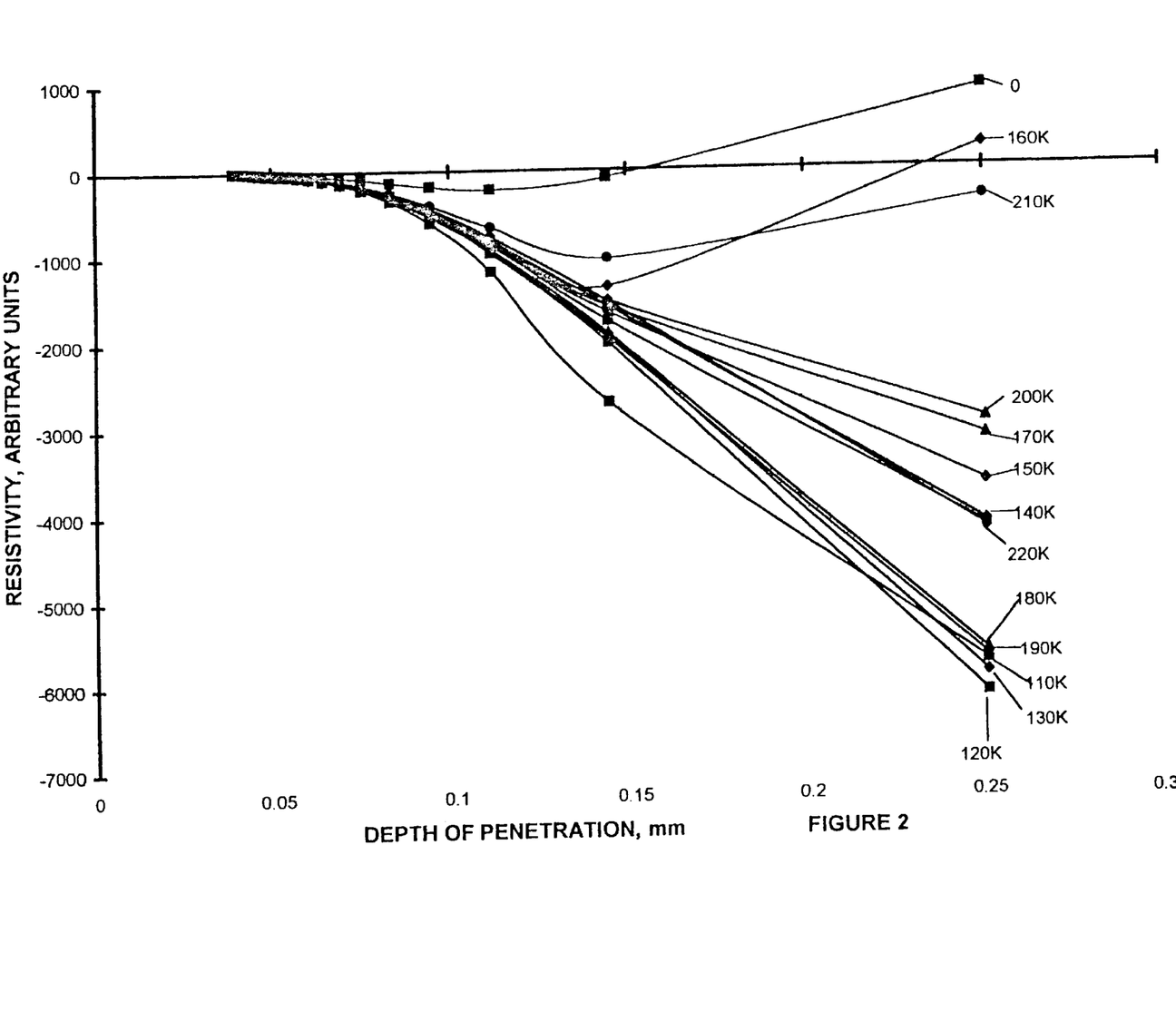
FIG. 2 is a graph in which changes in conductivity due to fatigue in a plate of 2024 aluminum are plotted against depth of penetration.

To more easily interpret these data, they were subjected to a mathematical transformation which corrects for the excessive dependence on frequency. Referring to FIG. 2, the voltage data is plotted as a function of $(1/f^{1/2})$, where "f" is frequency, which is proportional to the "standard depth of penetration" of the eddy currents. The ordinate is numerical because it shows the effect of converting voltages into numbers with an algorithm. The algorithm was developed from equations set forth in *Static and Dynamic Electricity*, 3rd Ed., by Wm. R. Smythe, McGraw Hill Book Co., New York 1968, Chapter X, pp 368–414 and *Principles of Electricity and Magnetism*, 2nd Ed. by Gaylord P. Harnwell, McGraw Hill Book Co., New York 1949, pp 340–350.

With the curves for successive sets of cycles plotted as in FIG. 2, it is seen that the initial values obtained on an "as-received" plate of 2024 aluminum, after 2 cycles (the effect of which is not measurable), at the beginning of the experiment, in a curve identified as "0". This curve is substantially coincident with the horizontal through "0", the reference. The plate is then subjected to 100,000 cycles and the conductivities at the various depths are measured and plotted in a curve identified as "100K", measurements after 100K cycles being recorded because it was expected that fatigue would likely begin to be evidenced not long thereafter. After 100K cycles, for a depth of penetration of 0.25 mm, the value obtained is about −4250.

Making all further comparisons at the same depth of penetration of 0.25 mm, it is seen that after 120K cycles, the value obtained is about −6200 indicating a much greater residual stress than after 100K cycles. After 160K cycles, the surface appears to have relaxed as the value obtained is about +200, close to the value for the reference. After 170K cycles, the surface shows a value of about −3000, a much higher value than obtained at 160K. After 200K cycles, the surface shows little change from the value obtained after 170K. Soon thereafter, after 210K cycles, the value obtained is about −500, not very different from the value for the reference. But after 220K cycles, the value obtained is about −4250, substantially different from the value for 200K and essentially the same as the values for 100K and 140K.

It is evident from the data presented in FIG. 2, that fatigue, as measured by differences in conductivity, cannot be predicted by knowing the number of cycles to which the specimen has been subjected.

It will be appreciated that the foregoing conclusion is derived from values for a depth of 0.25 mm which are read for ease and convenience. Essentially the same conclusion is reached by reading the values at any other depth, whether 0.15 mm or 0.1 mm, etc., the reliability with which the values may be read being a function of the ability to resolve the data at that depth.

In the second set of data presented herein, a comparison of resistivities is presented between measurements made on the surface of an unstressed "standard" 2024 aluminum plate, which is stress-relieved and not shot-peened, used as the reference, and, a plate of the same material which is shot-peened to provide a superficial compressive stress. For the experiment only a portion of the 2024 plate is shot-peened, as described above, to a 9A intensity per MIL13165C.

The conductivities in the shot-peened portion are measured at chosen frequencies (depths), and found to be lower than that of the "standard" (that is, the resistivity is higher than that of the standard), reflecting the effect of the build-up of residual stress in the near-surface of the stressed sample.

The plate is held, as described above, in the test machine and subjected to 30,000 cycle increments; the conductivity in the stressed portion is measured after each set of cycles. The differences in conductivities (or resistivities) between the stressed portion of the test specimen and the unstressed, stress-relieved standard plate are computed. It is found that the difference in resistivities between the additionally stressed state (greater number of cycles) and the "standard" in the non-stressed state, decreases progressively as the plate succumbs to fatigue.

Figure 3:
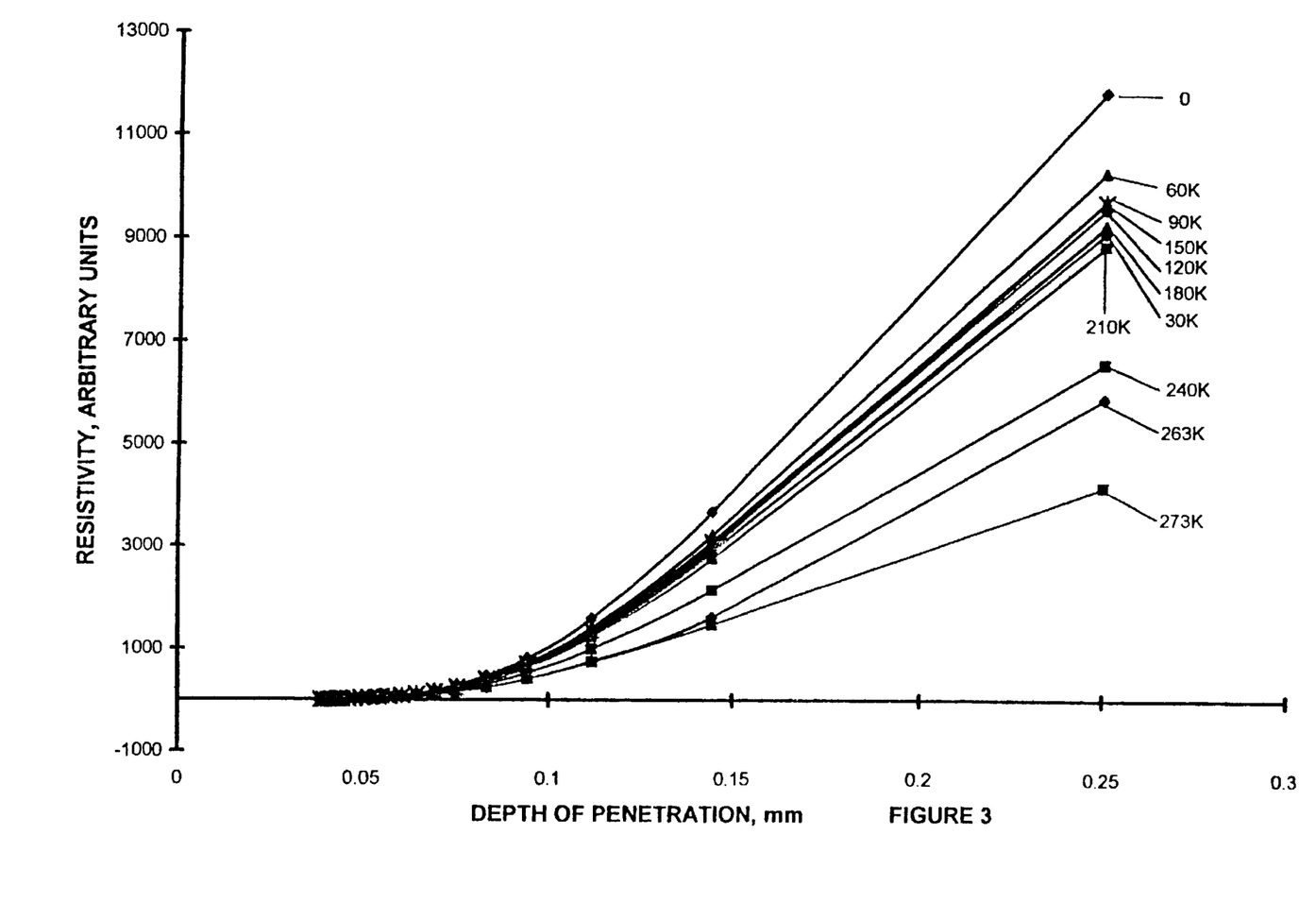
FIG. 3 is a graph in which changes in resistivity (arbitrary units) are plotted against standard depth of penetration for a plate of 2024 aluminum a portion of which was first shot-peened to approximately a 9A intensity per MIL13165C.

Referring to FIG. 3, the difference in conductivities is plotted as resistivity in arbitrary units, as a function of depth of penetration (corresponding to each frequency used), for the test specimen of shot-peened 2024 aluminum plate after it has been progressively subjected to 273K cycles in sequential 30,000 cycle sets after each of which measurements are made and recorded. After 273K cycles, large cracks were visible under the microscope at 100× indicating fatigue failure, and the test was discontinued.

The first measurements are made on the shot-peened plate at the beginning of the experiment. The conductivity is measured at various depths and identified by the curve identified as "0". As in the comparison presented in FIG. 2, the measured conductivity at a depth of 0.05 mm, at the beginning of the experiment, for comparison purposes, is assigned a value of zero, which is also the assigned value of the reference.

The plate is then subjected to 30,000 cycles and the conductivities at the various depths are measured and plotted in a curve identified as "30K". Thereafter, the plate is subjected to additional 30,000 cycle increments for which conductivities are plotted in successive curves which are appropriately identified. The data are obtained as a parametric representation of in-phase and out-of-phase signals, in microvolts, the independent variable being frequency, as before. In FIG. 3, standard depth of penetration is plotted along the abscissa because it is a function of frequency; and only the in-phase signal is used to derive the difference in resistivities which is proportional to the difference in the in-phase signal. This difference in resistivities is presented in arbitrary units as an artifact of an algorithm in which the data are mathematically manipulated using equations set forth in the aforementioned texts.

The general method for determining the difference in residual stress after a ferromagnetic or non-ferromagnetic specimen has been subjected to successive levels of stress, e.g. after one set of cyclical loading as compared to the level of stress after a previous set, each level of stress being measured relative to an unstressed surface of a "standard" specimen, is described in the '302 patent the disclosure of which is incorporated by reference thereto as if fully set forth herein.

Briefly, four identical induction coils are used; simultaneously, two of the coils are placed in contact with the stressed surface of the specimen where residual stress is to be measured; and, two of the coils are placed on the surface of a "standard" unstressed (stresses have been relieved) specimen. The coils are arranged geometrically to have non-interacting magnetic fields, and form a four terminal balanced alternating bridge circuit. A double pole double throw reversing switch is connected to two diagonally opposite coil terminals. Two diagonally opposite coil terminals are connected to a variable frequency constant voltage generator. Two of the diagonally opposite coil terminals are connected to a low noise broad band preamplifier to amplify any unbalance in the bridge.

The preamplifier is connected to an amplifier which is connected to a phase detector which is connected to a computer having several software programs. After the connections are made, the bridge is energized in the frequency range of 10 kHz to 200 MHz causing current to flow in the coils.

Lower frequencies penetrate the metal object more deeply than higher frequencies. The current is held to a few milliamperes to produce a field of $10^{-4}$ Tesla or less for a ferromagnetic object. The phase detector detects an in-phase component signal and a quadrature-component signal when the bridge is in a nearly symmetrical configuration. If all the circuit elements and the samples were ideal the bridge would be perfectly balanced. In practice a small error signal is detected due to slight differences in the test coil and/or sight point to point variations in the samples. Next the coils are interchanged using the double pole double throw reversing switch. The interchanging of the coils by exchanging a coil on a treated (worked) metal object with a coil on the untreated ("standard") metal object produces a maximum asymmetry in the bridge configuration.

After the interchange of the coils, the bridge is energized in a frequency range of 10 kHz to 200 MHz causing current to flow in the coils. The next step is detecting the in-phase component and quadrature component of the unbalanced signals when the bridge is in the asymmetrical configuration. The values secured for the in-phase and quadrature components from energizing the coils while in the nearly symmetric configuration are subtracted from the value secured while the coils are in the asymmetric configuration. These values are a function of specific frequencies. Software is used to determine the changes in differential resistivity, and convert the resistivity changes between the treated and untreated metal objects into residual stress in the treated metal object using an algorithm. This method can be used on the entire surface of the metal object, point by point to determine the extent to which the metal object has been worked, and the distribution of residual stress as a function of depth in the metal object over its worked surface.

Illustrative example:

Four identical induction coils each having the same induction in the range from about 15 $\mu$H to 30 $\mu$H (microHenries), and small footprint in the range from about 0.95 cm (0.375 in) to 2.54 cm (1") in diameter, are used to sample an appropriately small region of a surface. Two of the coils are placed on regions of the worked 2024 aluminum specimen, each of which regions are known to have essentially identical metallurgical properties, i.e. shot-peened to the same extent, crystal structure and the like. Two of the induction coils are placed on the "standard" sample to serve as reference coils. The standard aluminum sample is stress-relieved by heating to about 121° C. (250° F.) for one hour and slowly cooling the sample to room temperature.

The inductance of a pair of coils is adjusted to be identical within the range from 0.0005% to 0.005%, preferably in the range from 0.001% to 0.002%.

The signal is amplified in a phase lock detector which reports both the amplitude and the phase of the signal from the bridge. It is this amplitude and phase information from which the difference in resistivities is deduced by application of an algorithm.

Reverting to FIG. 3, data for the uppermost curve "0" were taken on the shot-peened plate at the beginning of the experiment. The effect of the shot-peening is clear. After being stressed for 30,000 cycles (curve 30K), the surface conductivity increased substantially, that is, the resistivity decreased substantially. After being stressed for 60,000 cycles (curve 60K), the surface conductivity decreased further, that is, the resistivity increased substantially. Note however, that after 30K cycles the resistivity value decreased to about 9000 which is substantially below the initial about value of about 12000. Values for 60K, 90K, 120K and 150K cycles were higher than the value for 30K cycles. This behavior was similar to that seen in FIG. 2 for the unpeened plate.

After 60,000 cycles the resistivity continued to decrease slowly, remaining nearly constant in the range from about 90,000 to 150,000 cycles (curves 90K–150K). A rapid decrease began after about 150,000 cycles and continued to 273,000 cycles. The surface resistivity at time of failure had declined to about 30% of its initial value. More importantly, the 150,000 cycle data, which represents about 55% of the ultimate fatigue life, show the resistivity had declined to about 50% from its initial value. Beyond this point one would be justified in declaring further loading and unloading of the test specimen unsafe, and to refer to this point as corresponding to the "safe-operation" point. Though most readily visible for values at a depth of 0.25 mm, essentially the same conclusion is derived from data at another depth. Removing the test specimen from further service promptly after the "safe-operation" point, though well before actual fatigue failure, avoids the risk of that failure.

Having thus provided a general discussion, described the overall process in detail and illustrated the invention with specific examples of the best mode of carrying out the process, it will be evident that a solution to a difficult and long-standing problem has been provided. It is therefore to be understood that no undue restrictions are to be imposed by reason of the specific embodiments illustrated and discussed, and particularly that the invention is not restricted to a slavish adherence to the details set forth herein.

I claim:

1. A method of determining a "safe-operation" point of a first metal structural element having a near-surface which is strained, comprising, measuring and comparing at least one property of the near-surface to determine a first difference between a first measurement of residual stress in the near-surface of the first metal structural element, and, a reference measurement of a reference residual stress in a standard metal structural element having essentially the same metallurgical properties as the first when each is stress-relieved;

repetitively loading the first metal structural element; measuring and comparing the property of the near-surface to determine differences between each measurement of residual stress in the near-surface of the first metal structural element after each loading, and the reference measurements at corresponding depths in the near-surface; and, determining the 50% safe-operation point for the first structural element corresponding to an Nth loading for which the difference between the residual stress at the Nth loading and the residual stress in the standard reference metal structural element is in the range from about 50% to 60% of the first difference.

2. The method of claim 1 wherein the near-surface of the metal structural element is a superficial zone having a depth in the range from about 0.025 mm (0.001") to 0.5 mm (0.020").

3. The method of claim 1 including, prior to making the first measurement, peening the near-surface to a depth in the range from about 0.127 mm (0.005") to 0.5 mm (0.020").

4. The method of claim 1 wherein the first measurement and the reference measurement are made and compared with X-rays.

5. The method of claim 1 wherein the first measurement and the reference measurement are made and compared as electrical conductivities.

6. The method of claim 1 wherein the metal structural element is formed from a metal susceptible to an increase in residual stress when peened.

7. The method of claim 5 wherein the first measurement and the reference measurement are made by generating eddy currents in the near-surface.

8. The method of claim 5 including detecting a change in conductivity corresponding to a change in impedance in the range from 0.01 to 0.001 percent.

9. The method of claim 1 including, in addition, removing the structural element from further service.

10. A method of determining a safe-operation point of a first metal structural element having a near-surface which is strained, prior to imminent failure, comprising, working the element sufficiently to produce a measurable first residual stress and measuring the effect of the residual stress;

measuring the effect of a second residual stress in a standard reference metal structural element having essentially the same metallurgical properties as the first when each is stress-relieved, to provide a basis for comparison;

measuring the difference in residual stresses between the first residual stress in the first structural element, and, the second residual stress in the standard reference metal structural element to obtain a first difference;

subjecting the first structural element to a load sufficient to increase residual stress corresponding to a third residual stress and measuring a second difference in residual stresses between the third residual stress and the residual stress in the standard reference metal structural element;

continuing to subject the first structural element to a load sufficient to increase the residual stress corresponding to increased loading and measuring the difference in residual stresses between residual stress at a chosen loading and the residual stress in the standard reference metal structural element; and, determining the 50% "safe-operation" point for the first structural element corresponding to an Nth loading for which the difference between the residual stress at the Nth loading and the residual stress in the standard reference metal structural element is in the range from about 50% to 60% of the first difference.

11. The method of claim 10 wherein the near-surface of the metal structural element is a superficial zone having a depth in the range from about 0.025 mm (0.001") to 0.5 mm (0.020").

12. The method of claim 11 wherein working is provided by peening the near-surface to a depth in the range from about 0.127 mm (0.005") to 0.5 mm (0.020").

13. The method of claim 10 wherein residual stresses are compared as electrical conductivities.

14. The method of claim 10 wherein the metal structural element is formed from a metal susceptible to an increase in residual stress when peened.

15. The method of claim 13 wherein the residual stresses are compared by generating eddy currents in the near-surface.

16. The method of claim 15 including detecting a change in conductivity corresponding to a change in impedance in the range from 0.01 to 0.001 percent.

17. A method of non-destructively testing a first metal structural element having a near-surface which is strained, to determine its "safe-operation" point prior to imminent failure, comprising, working the element sufficiently to produce a residual stress measurable as a first electrical conductivity in the element's near-surface, and measuring the first conductivity;

measuring the conductivity of a standard reference metal structural element having essentially the same metallurgical properties as the first when each is stress-relieved, as a reference conductivity;

measuring a first difference between the first conductivity and the conductivity of the standard;

subjecting the first structural element to a load sufficient to increase residual stress and decrease conductivity corresponding to a second residual stress, and measuring the decreased conductivity;

measuring a second difference in conductivities between the second conductivity and the reference conductivity;

continuing to subject the first structural element to a load sufficient to increase the residual stress corresponding to successive increased loadings and continued decreasing conductivities;

measuring the conductivities at chosen loadings;

measuring the differences between conductivities at a chosen loading and the reference conductivity until an Nth loading for which the difference between the conductivity at the Nth loading and the reference conductivity is in the range from about 50% to 60% of the first difference.

18. The method of claim 17 wherein working is provided by peening the near-surface to a depth in the range from about 0.127 mm (0.005") to 0.5 mm (0.020").

19. The method of claim 17 wherein the metal structural element is formed from a metal susceptible to an increase in residual stress when peened.

20. The method of claim 20 wherein the first measurement and the reference measurement are made by generating eddy currents in the near-surface.

* * * * *